United States Patent
Shi et al.

(10) Patent No.: US 8,414,479 B2
(45) Date of Patent: Apr. 9, 2013

(54) CAPSULE ENDOSCOPE

(75) Inventors: Bin Shi, Hong Kong (CN); Xing Quan Li, Shenzhen (CN); Liang Guan, Shenzhen (CN)

(73) Assignee: Johnson Electric S.A., La Chaux-de-Fonds (CH)

( * ) Notice: Subject to any disclaimer, the term of this patent is extended or adjusted under 35 U.S.C. 154(b) by 728 days.

(21) Appl. No.: 12/631,558

(22) Filed: Dec. 4, 2009

(65) Prior Publication Data

US 2010/0145145 A1  Jun. 10, 2010

(30) Foreign Application Priority Data

Dec. 5, 2008  (CN) .......................... 2008 1 0218100

(51) Int. Cl.
*A61B 1/06* (2006.01)

(52) U.S. Cl. ..................................... 600/160; 600/173

(58) Field of Classification Search .................. 600/109, 600/118, 160, 173, 179
See application file for complete search history.

(56) References Cited

U.S. PATENT DOCUMENTS

| | | | |
|---|---|---|---|
| 5,604,531 A | 2/1997 | Iddan et al. | |
| 6,428,470 B1 * | 8/2002 | Thompson | 600/173 |
| 6,666,833 B1 * | 12/2003 | Friedman et al. | 601/2 |
| 7,244,229 B2 | 7/2007 | Yokoi et al. | |
| 7,465,271 B2 | 12/2008 | Kanazawa | |
| 7,625,338 B2 | 12/2009 | Gilad et al. | |
| 7,801,584 B2 * | 9/2010 | Iddan et al. | 600/407 |
| 8,088,065 B2 * | 1/2012 | Karasawa et al. | 600/157 |
| 2003/0171652 A1 | 9/2003 | Yokoi et al. | |
| 2005/0043588 A1 * | 2/2005 | Tsai | 600/160 |
| 2005/0143644 A1 | 6/2005 | Gilad et al. | |
| 2006/0004253 A1 | 1/2006 | Shigemori et al. | |
| 2006/0217593 A1 * | 9/2006 | Gilad et al. | 600/160 |
| 2007/0185381 A1 * | 8/2007 | Kimoto et al. | 600/117 |
| 2007/0282169 A1 | 12/2007 | Tsujita | |
| 2008/0021281 A1 | 1/2008 | Fujimori | |
| 2008/0200757 A1 * | 8/2008 | Glukhovsky et al. | 600/109 |
| 2010/0016673 A1 * | 1/2010 | Bandy et al. | 600/178 |
| 2011/0098530 A1 * | 4/2011 | Yamane | 600/109 |

FOREIGN PATENT DOCUMENTS

| | | |
|---|---|---|
| JP | 2007-159641 | 6/2007 |
| JP | 2007-159642 | 6/2007 |

* cited by examiner

*Primary Examiner* — Christopher Mahoney
(74) *Attorney, Agent, or Firm* — Muncy, Geissler, Olds & Lowe, PLLC

(57) ABSTRACT

A capsule endoscope includes an enclosure with a transparent section, a illumination unit arranged to illuminate an object to be observed via the transparent section, an image unit disposed in the enclosure, a reflecting unit disposed in the enclosure and arranged to direct light from the object to the image unit to form an image of the object, and a driving unit comprising a piezoelectric motor arranged to rotate the reflecting unit relative to the enclosure.

15 Claims, 4 Drawing Sheets

CAPSULE ENDOSCOPE

CROSS REFERENCE TO RELATED APPLICATIONS

This non-provisional patent application claims priority under 35 U.S.C. §119(a) from Patent Application No. 200810218100.6 filed in The People's Republic of China on Dec. 5, 2008.

FIELD OF THE INVENTION

This invention relates to the field of medical image technology and in particular, to a capsule endoscope.

BACKGROUND OF THE INVENTION

Endoscopes have been widely used in the medical and industrial fields. Recently, endoscopes have been developed which are to be swallowed by the patient and the images relayed to equipment outside of the patient by wireless means. These endoscopes have been miniaturized and placed within a capsule, as shown for example in U.S. Pat. Nos. 5,604,531 & 7,244,229. After the being swallowed the capsule travels passively down the esophagus, through the stomach and through the small and large intestines and bowel before leaving the body naturally. During its travels through the body, the endoscope captures a plurality of images of the organs it passes through.

In the known capsule endoscopes, the optical lens and illumination unit are installed at the transparent front end of the capsule enclosure and fixed relative to the enclosure. Thus, the capsule endoscopes are only able to capture images of objects located at the front side thereof. However, when a doctor observes an organ of a patient, the doctor is more interested in the images of inner sidewalls of the organ. It is difficult to get images of sidewalls of an organ when using the known capsule endoscopes.

SUMMARY OF THE INVENTION

Hence there is a desire for an improved capsule endoscope.

Accordingly, in one aspect thereof, the present invention provides a capsule endoscope comprising: an enclosure with a transparent section located between opposite ends thereof; an illumination unit arranged to illuminate an object to be observed via the transparent section; an image unit disposed in the enclosure; a reflecting unit disposed in the enclosure and arranged to form an image of the object on the image unit; and a driving unit configured to move the reflecting unit relative to the enclosure.

Preferably, the endoscope has a communication unit configured to transmit an image signal of the object from the image unit to external apparatus.

Preferably, the reflecting unit comprises a reflector mirror and a support seat supporting the reflector mirror.

Preferably, the driving unit comprises a piezoelectric motor configured to rotate the support seat together with the reflector mirror relative to the enclosure.

Preferably, the support seat comprises a cylindrical body and a slant mirror support part fixed relative to the body, the piezoelectric motor comprises a nub resiliently pressed against the body in a direction parallel to the axial direction or a radial direction of the body under the urging of an elastic member.

Preferably, the body has a hollow form and the piezoelectric motor is installed inside the body and the nub is resiliently pressed against an inner surface of the body in a radial direction of the body.

Alternatively, the body is a round plate and the nub of the piezoelectric motor resiliently pressed against the round plate in a direction parallel to the axial direction of the plate.

Alternatively, the body is a hollow tube and the reflector mirror is disposed within the tube, and the nub of the piezoelectric motor is resiliently pressed against an axial end of the tube in a direction parallel to the axial direction of the tube.

Preferably, the piezoelectric motor is mounted in a motor seat which is attached to a base fixed relative to the enclosure.

Preferably, the enclosure comprises a tubular part and a pair of semi-spherical end parts formed at opposite ends of the tubular part, the transparent section being formed in the tubular part and facing the reflector mirror.

Preferably, the image unit comprises a zoomable lens module.

According to a second aspect, the present invention provides an image capture system configured to capture the image of an object within a human or animal body, the image capture system comprising the capsule endoscope mentioned above adapted to be swallowed into the body and an external apparatus, the capsule endoscope being configured to capture the image of the object and transmit image signals to the external apparatus which is configured to receive the image signal and/or display the images.

Preferably, the capsule endoscope provides raw image data to the external apparatus which processes the raw image data to produce 3D images of the object being observed.

BRIEF DESCRIPTION OF THE DRAWINGS

Preferred embodiments of the invention will now be described, by way of example only, with reference to figures of the accompanying drawings. Dimensions of components and features shown in the figures are generally chosen for convenience and clarity of presentation and are not necessarily shown to scale. The figures are listed below.

DETAILED DESCRIPTION OF THE PREFERRED EMBODIMENTS

Figure 1:
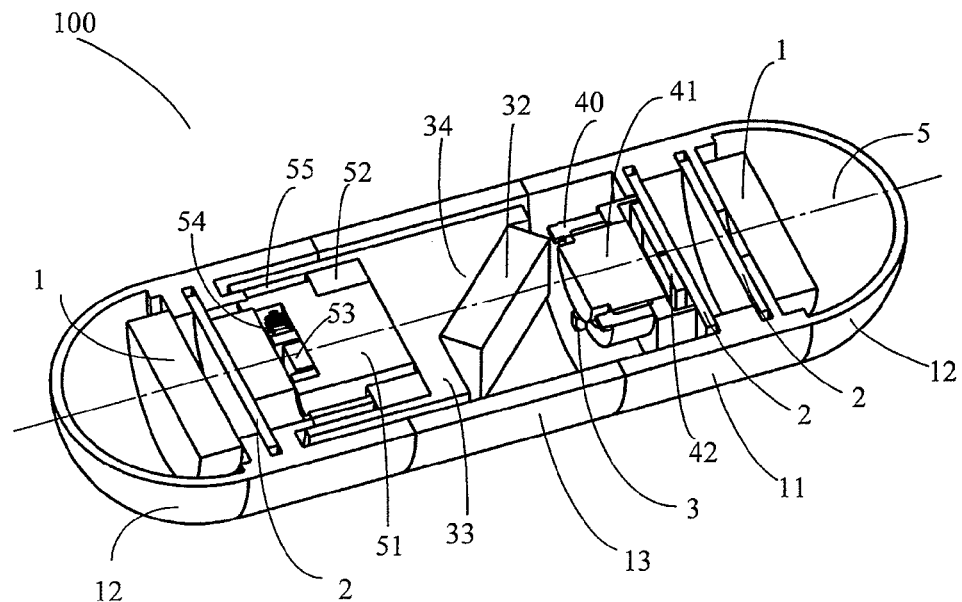
FIG. 1 is a sectional view showing the internal configuration of a capsule endoscope according to a first embodiment of the present invention.
Figure 2:
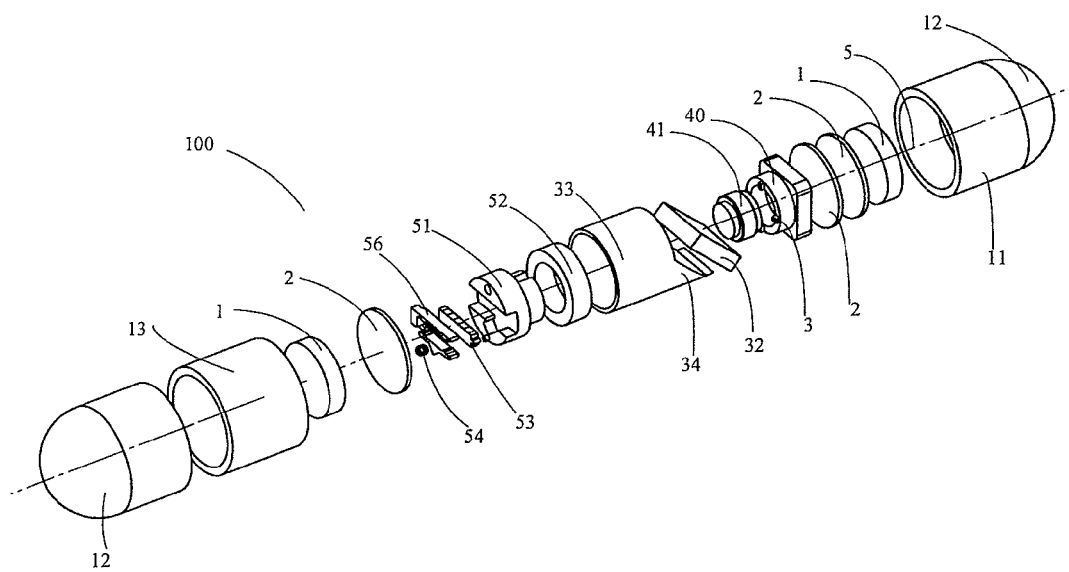
FIG. 2 is an exploded view of the capsule endoscope of FIG. 1.
Figure 3:
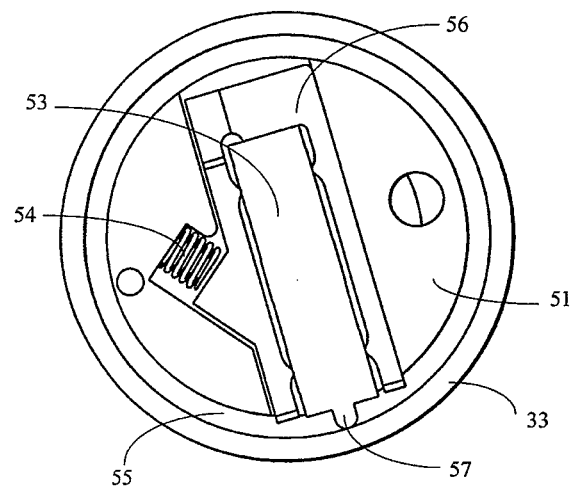
FIG. 3 is a plan view showing a piezoelectric motor installed in the main body of a support seat, being parts of the endoscope of FIG. 1.

Referring firstly to FIG. 1 to FIG. 3, a capsule endoscope 100 according to a first embodiment of the present invention comprises an enclosure housing a power source 1, one or more circuit boards 2, an illumination unit 3, a reflecting unit, an imaging unit, and a driving unit.

The enclosure comprises a tubular part 11 and a pair of semi-spherical end parts 12 formed at opposite ends of the tubular part 11. The tubular part 11 comprises a transparent section 13.

The illumination unit 3 may comprise a plurality of luminescent components, such as luminescent diodes or light emitting diodes. The illumination unit 3 is arranged to illuminate an object to be observed through the transparent section 13 of the tubular part 11.

The reflecting unit comprises a reflector mirror 32 and a mirror support seat for supporting the mirror 32. The support seat comprises a cylindrical body 33 and a slant mirror support part 34 extending from one end of the body 33. The cylindrical body 33 is coaxial with the enclosure, i.e., the central axis 5 of the enclosure extending through the center of the cylindrical body 33. The slant mirror support part 34 has a slant surface angled to the axis 5. The mirror 32 is secured on the slant surface and arranged to face the transparent section 13 of the tubular part 11, to reflect light from the object to be observed passing through the transparent section 13 of the tubular part 11 to the imaging unit. The end of the cylindrical body 33 remote from the mirror 32 forms an opening for receiving the driving unit.

The imaging unit comprises a frame 40, an object lens 41 mounted to the frame 40, an image sensor 42. The object to be observed is illuminated by the illumination unit 3 and the mirror 32 forms an image of the object on the image sensor 42. The optical axis of the object lens 41 and the central axis 5 of the enclosure may be collinear, and the mirror 32 may be at an angle of 45 degrees to the optical axis of the object lens 41. The image sensor 42 may be of CCD or CMOS type. The illumination unit 3 may be arranged at the frame 40 around the object lens 41.

The driving unit comprises a base 51 fixed relative to the enclosure, a piezoelectric motor 53, an elastic member 54, and a motor seat 56 defining a groove for receiving the motor 53 therein. The base 51 is accommodated in the opening of the cylindrical body 33 of the support seat with a bearing 52 arranged between the base 51 and the cylindrical body 33 such that the body 33 is rotatable relative to the base 51. The elastic member 54 is configured to resiliently bias the piezoelectric motor 53 to cause a friction nub 57 of the motor 53 to resiliently press against the inner surface of the cylindrical body 33. When the piezoelectric motor 53 is energized the piezoelectric motor 53 will rotate the cylindrical body 33 together with the mirror 32 about the axis 5 relative to the enclosure.

Driving circuits for the illumination unit, imaging unit, and piezoelectric motor 53 are mounted on the circuit boards 2. A communication unit configured to transmit wirelessly image signals from the image unit to external apparatus may be installed on the circuit boards 2. The power source 1 such as a battery is arranged to supply power to the driving circuits.

Optionally piezoelectric motor 53 is a type of motor described in U.S. Pat. No. 5,453,653, the disclosure of which is incorporated herein by reference. The motor comprises a thin rectangular ceramic piezoelectric vibrator having front and back planar face surfaces, relatively long edge surfaces and relatively short top and bottom edge surfaces. The friction nub is located on a short edge of the vibrator. Four quadrant electrodes are located in a symmetric checkerboard pattern on the front face surface. A single large electrode is located on the back surface. A controller electrifies quadrant electrodes to generate vibrations in the vibrator of piezoelectric motor and thereby in friction nub to apply force to the body 33 of the support seat and generate torque that rotates the support seat together with mirror 32 selectively clockwise or counter clockwise about the axis 5. In this embodiment, the controller of the piezoelectric motor 53 electrifies the electrodes of the piezoelectric motor when receiving a command from the external apparatus.

Alternatively, the piezoelectric motor 53 may also be a type of piezoelectric motor disclosed in US2008/0073999A1, the disclosure of which is incorporated herein by reference. The piezoelectric motor comprises an oscillator in the form of a piezoelectric plate of the length L and the height H as well as with one or two friction elements which are arranged on the oscillator and resiliently pressed against the friction surface of the part to be moved. The piezoelectric plate is divided into two identical parts by a section plane extending vertically to the large surfaces, with at least one of these parts including an asymmetrical generator of an asymmetrical acoustic standing wave, which upon its activation generates an asymmetrical two-dimensional standing wave, so that the friction elements which are arranged in the centre of the long end face of the plate carry out a movement with an inclination relative to the end face, so that the energy of motion is transferred to the element to be moved.

Figure 4:
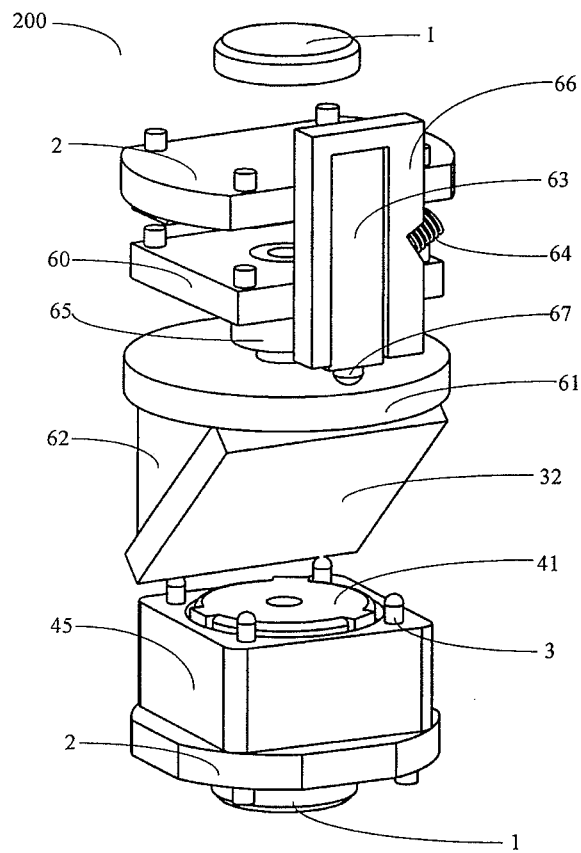
FIG. 4 is an isometric view of a capsule endoscope according to a second embodiment of the present invention, the enclosure of the capsule endoscope being omitted to show the internal mechanism of the capsule endoscope.
Figure 5:
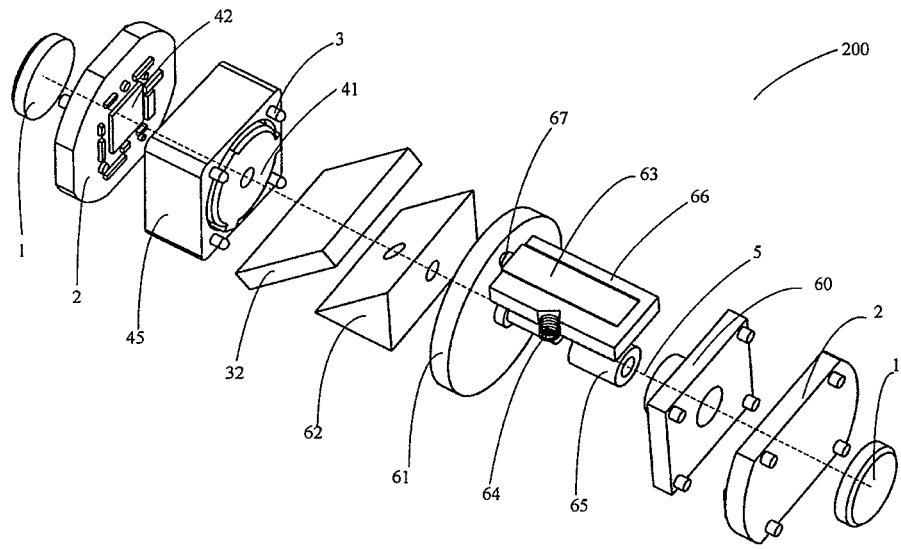
FIG. 5 is an exploded view of the internal mechanism of the capsule endoscope of FIG. 4.

FIGS. 4 and 5 show another capsule endoscope 200 according to a second embodiment of the present invention. The capsule endoscope 200 is similar to the capsule endoscope 100 except that the reflecting unit is pivotably mounted to a support bracket 60 which is fixed relative to the enclosure, the mirror support seat comprises a round plate 61 and a slant mirror support part 62 extending from one side of the plate 61 for supporting the mirror 32 thereon, a shaft extends from the opposite side of the plate 61 and pivotally supported in a bearing 65 which is fixed into an opening of the bracket 60, the motor seat 66 is disposed at the opposite side of the plate 61, the elastic member 64 urges the motor seat 66 to cause the nub 67 of the piezoelectric motor 63 to elastically press against the opposite side surface of the plate 61. When the piezoelectric motor 63 is energized the nub 67 of the piezoelectric motor 63 will rotate the plate 61 together with the mirror 32 about the axis 5 relative to the enclosure.

FIG. 5 shows more details of the image unit which comprises a lens module 45 with the object lens 41 and an image sensor 42. The illumination diodes 3 are arranged at the periphery of the lens module 45 surrounding the object lens 41. The illumination diodes 3 illuminate the object to be observed near the transparent section 13 (shown in FIG. 1) of the enclosure and the reflector mirror 32 reflects light from the object through the object lens 41 to form images of the object on the image sensor 42. Lens holders and driving devices for automatically adjusting focus of the lens may be installed within the lens module 45.

Figure 6:
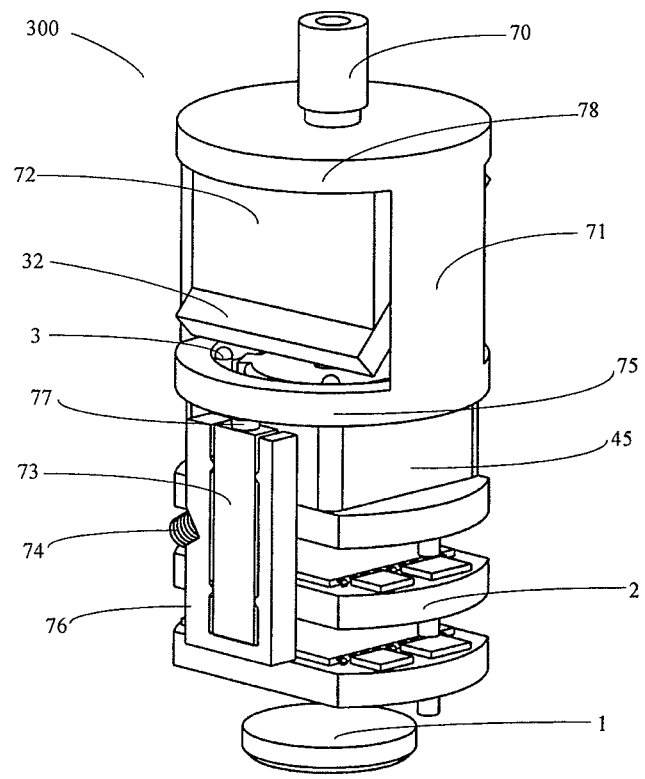
FIG. 6 is an isometric view of a capsule endoscope according to a third embodiment of the present invention, the enclosure of the capsule endoscope being omitted to show the internal mechanism.
Figure 7:
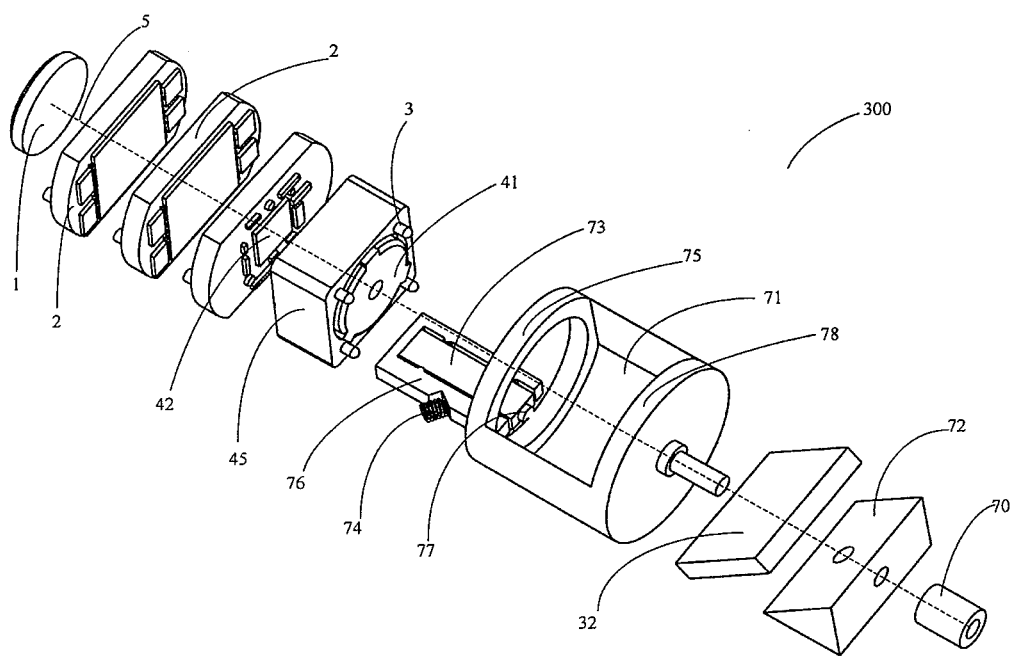
FIG. 7 is an exploded view of the internal mechanism of the capsule endoscope of FIG. 6.

FIGS. 6 and 7 show a third capsule endoscope 300 according to a third embodiment of the present invention. The difference between the third capsule endoscope 300 and the first capsule endoscope 100 is that in the third capsule endoscope 300 the reflecting unit is installed inside the hollow cylindrical body 71 of the support seat. The cylindrical body 71 has an opening facing the mirror 32 which is fixedly installed in the hollow cylindrical body 71 by the mirror seat 72. The support seat is pivotably attached to the enclosure by bearing 70. One end 75 of the cylindrical body 71 adjacent the image unit is open to allow the reflected light from the mirror 32 to pass there through to reach the image unit. The motor seat 76 is arranged in such a manner that the nub 77 of the piezoelectric motor 73 axially and resiliently pressed against the axial surface of the end 75 of the cylindrical body 71 under the pressure of the elastic member 74. When the piezoelectric motor 73 is energized the nub 77 of the piezoelectric motor 73 will cause the cylindrical body 71 together with the mirror 32 to rotate about the central axis 5 relative to the enclosure.

The present invention further provides an image capture system configured to capture the image of an object within a human or animal body. The image capture system comprises a capsule endoscope which adapted to be swallowed to enter the body and an external apparatus. The capsule endoscope is configured to capture the image of the object and transmit image signals of the object to the external apparatus which is configured to receive the image signals and/or display the images. The capsule endoscope may be any one of the capsule endoscopes described herein before. The image signals transmitted from the capsule endoscope are wireless signals. The external apparatus has a receiving unit configured to receive the image signals from the capsule endoscope, a storage unit configured to store the image data, and/or a display unit configured to display the images. The external apparatus may further connect to a computer via a cable such that images stored in the external apparatus can be transferred to the computer, where they may be variously processed for displaying, stored in a suitable manner such as a hard disk, and/or displayed.

In the present invention, the reflector mirror is rotatable relative to the enclosure such that the capsule endoscope is capable of capturing the image of an object to be observed in a variety of aspects. Furthermore, the capsule endoscope adapts the piezoelectric motor to drive the reflector mirror, which is not affected by an outside magnetic field and does not generate a magnetic field. Thus it can be used in conjunction with other medical devices which use or are sensitive to magnetic fields.

In the description and claims of the present application, each of the verbs "comprise", "include", "contain" and "have", and variations thereof, are used in an inclusive sense, to specify the presence of the stated item but not to exclude the presence of additional items.

Although the invention is described with reference to one or more preferred embodiments, it should be appreciated by those skilled in the art that various modifications are possible. Therefore, the scope of the invention is to be determined by reference to the claims that follow.

For example, the image unit is described as being capable of autofocusing but it could also be able to zoom in to the object being observed and the external computer apparatus could be used to generate 3D images from the raw images gathered by the image unit.

The invention claimed is:

1. A capsule endoscope comprising:
   an enclosure with a transparent section located between opposite ends thereof;
   an illumination unit arranged to illuminate an object to be observed via the transparent section;
   an image unit disposed in the enclosure;
   a reflecting unit disposed in the enclosure and arranged to form an image of the object on the image unit; and
   a driving unit configured to move the reflecting unit relative to the enclosure;
   wherein the reflecting unit comprises a reflector mirror and a support seat supporting the reflector mirror, the driving unit comprises a piezoelectric motor configured to rotate the support seat together with the reflector mirror relative to the enclosure, the support seat comprises a cylindrical body, and the piezoelectric motor comprises a nub resiliently pressed against the body.

2. The capsule endoscope of claim 1, further comprising a communication unit configured to transmit an image signal of the object from the image unit to external apparatus.

3. The capsule endoscope of claim 1, wherein the piezoelectric motor is mounted in a motor seat which is attached to a base fixed relative to the enclosure.

4. The capsule endoscope of claim 1, wherein the enclosure comprises a tubular part and a pair of semi-spherical end parts formed at opposite ends of the tubular part, the transparent section being formed in the tubular part and facing the reflector mirror.

5. The capsule endoscope of claim 1, wherein the image unit comprises a zoomable lens module.

6. An image capture system configured to capture the image of an object within a human or animal body, the image capture system comprising the capsule endoscope of claim 1 adapted to be swallowed into the body and an external apparatus, the capsule endoscope being configured to capture the image of the object and transmit image signals to the external apparatus which is configured to receive the image signal and/or display the images.

7. The image capture system of claim 6 wherein the capsule endoscope provides raw image data to the external apparatus which processes the raw image data to produce 3D images of the object being observed.

8. The image capture system of claim 1, wherein the support seat further comprises a slant mirror support part fixed relative to the body.

9. The capsule endoscope of claim 1, wherein the body has a hollow form and the piezoelectric motor is installed inside the body and the nub is resiliently pressed against an inner surface of the body.

10. The capsule endoscope of claim 1, wherein the body is a round plate and the nub of the piezoelectric motor resiliently pressed against the round plate in a direction parallel to the axial direction of the plate.

11. The capsule endoscope of claim 1, wherein the body is a hollow tube and the reflector mirror is disposed within the tube, and the nub of the piezoelectric motor is resiliently pressed against an axial end of the tube in a direction parallel to the axial direction of the tube.

12. A capsule endoscope comprising:
   an enclosure with a transparent section located between opposite ends thereof;
   an illumination unit arranged to illuminate an object to be observed via the transparent section;
   an image unit disposed in the enclosure;
   a reflecting unit disposed in the enclosure and arranged to form an image of the object on the image unit; and
   a driving unit configured to move the reflecting unit relative to the enclosure;
   wherein the reflecting unit comprises a reflector mirror and a support seat supporting the reflector mirror, the driving unit comprises a piezoelectric motor configured to rotate the support seat together with the reflector mirror relative to the enclosure, the support seat comprises a cylindrical body and a slant mirror support part fixed relative to the body, the piezoelectric motor comprises a nub resiliently pressed against the body in a direction parallel to the axial direction or a radial direction of the body under the urging of an elastic member.

13. The capsule endoscope of claim 12, wherein the body has a hollow form and the piezoelectric motor is installed inside the body and the nub is resiliently pressed against an inner surface of the body in a radial direction of the body.

14. The capsule endoscope of claim 12, wherein the body is a round plate and the nub of the piezoelectric motor resiliently pressed against the round plate in a direction parallel to the axial direction of the plate.

15. The capsule endoscope of claim 12, wherein the body is a hollow tube and the reflector mirror is disposed within the tube, and the nub of the piezoelectric motor is resiliently pressed against an axial end of the tube in a direction parallel to the axial direction of the tube.

* * * * *